United States Patent
Shener et al.

(10) Patent No.: US 7,150,713 B2
(45) Date of Patent: Dec. 19, 2006

(54) ENDOSCOPIC DEVICE

(75) Inventors: Cemal Shener, Woburn, MA (US); Scott M. Benedict, Nashua, NH (US)

(73) Assignee: Smith & Nephew, Inc., Memphis, TN (US)

( * ) Notice: Subject to any disclaimer, the term of this patent is extended or adjusted under 35 U.S.C. 154(b) by 335 days.

(21) Appl. No.: 10/685,590

(22) Filed: Oct. 16, 2003

(65) Prior Publication Data

US 2005/0085695 A1   Apr. 21, 2005

(51) Int. Cl.
A61B 1/015 (2006.01)
A61B 1/018 (2006.01)

(52) U.S. Cl. .............. 600/156; 600/104; 600/128; 600/129; 600/105; 600/561; 604/43

(58) Field of Classification Search .............. 600/105, 600/125, 128, 129, 135, 156–159, 114, 104, 600/561; 604/27, 31, 43, 65, 66, 118
See application file for complete search history.

(56) References Cited

U.S. PATENT DOCUMENTS

| | | | |
|---|---|---|---|
| 1,666,332 A | 4/1928 | Hirsch | |
| 3,900,022 A | 8/1975 | Widran | |
| 3,939,839 A * | 2/1976 | Curtiss | 606/46 |
| 3,996,921 A | 12/1976 | Neuwirth | |
| 4,369,768 A | 1/1983 | Vukovic | |
| 4,423,727 A | 1/1984 | Widran et al. | |
| 4,449,538 A | 5/1984 | Corbitt et al. | |
| 4,543,965 A | 10/1985 | Pack et al. | |
| 4,756,309 A | 7/1988 | Sachse et al. | |
| 4,924,851 A | 5/1990 | Ognier et al. | |
| 4,950,278 A | 8/1990 | Sachse et al. | |
| 4,955,882 A | 9/1990 | Hakky et al. | |
| 4,998,527 A | 3/1991 | Meyer | |
| 4,998,914 A | 3/1991 | Wiest et al. | |
| 5,037,386 A | 8/1991 | Marcus et al. | |
| 5,163,433 A | 11/1992 | Kagawa et al. | |
| 5,195,541 A | 3/1993 | Obenchain | |
| 5,257,617 A * | 11/1993 | Takahashi | 600/123 |
| 5,320,091 A | 6/1994 | Grossi et al. | |
| 5,392,765 A | 2/1995 | Muller | |
| 5,449,356 A | 9/1995 | Walbrink et al. | |
| 5,456,689 A | 10/1995 | Kresch et al. | |
| 5,483,951 A * | 1/1996 | Frassica et al. | 600/104 |

(Continued)

FOREIGN PATENT DOCUMENTS

DE   3601 453 A1   9/1986

(Continued)

OTHER PUBLICATIONS

Model 4355 cannula, "Cannula, Diagnostic, 4mm Arthroscopic," Dwg Nos. 8011379, 8011383, 8107369, 8011381, 8011385 5 pages, sold before Jun. 16, 1992.

(Continued)

*Primary Examiner*—John P. Leubecker
(74) *Attorney, Agent, or Firm*—Fish & Richardson P.C.

(57) ABSTRACT

An endoscopic device for use at a site within a body includes an inner portion and a sheath surrounding the inner portion. The inner portion defines an operative channel and an optical channel. The operative channel provides a path for fluid to or from the body site. The sheath defines a pressure-sensing channel and a fluid channel that provides a path for fluid to or from the body site. The pressure-sensing channel and the fluid channel are defined between the sheath and the inner portion. The pressure-sensing channel is configured to couple to a pressure sensor to sense pressure at the body site.

32 Claims, 9 Drawing Sheets

U.S. PATENT DOCUMENTS

| | | | |
|---|---|---|---|
| 5,492,537 A | | 2/1996 | Vancaillie |
| 5,498,258 A | | 3/1996 | Hakky et al. |
| 5,549,541 A | | 8/1996 | Muller |
| 5,556,378 A | | 9/1996 | Storz et al. |
| 5,569,254 A | | 10/1996 | Carlson et al. |
| 5,575,756 A | * | 11/1996 | Karasawa et al. .......... 600/157 |
| 5,603,332 A | | 2/1997 | O'Connor |
| 5,630,798 A | | 5/1997 | Beiser et al. |
| 5,637,075 A | * | 6/1997 | Kikawada ................... 600/153 |
| 5,730,752 A | | 3/1998 | Alden et al. |
| 5,749,885 A | | 5/1998 | Sjostrom et al. |
| 5,759,185 A | | 6/1998 | Grinberg |
| 5,772,634 A | | 6/1998 | Atkinson |
| 5,814,009 A | | 9/1998 | Wheatman |
| 5,840,060 A | | 11/1998 | Beiser et al. |
| 5,913,867 A | | 6/1999 | Dion |
| 5,944,654 A | * | 8/1999 | Crawford ................... 600/157 |
| 5,944,668 A | | 8/1999 | Vancaillie et al. |
| 5,947,990 A | | 9/1999 | Smith |
| 5,956,130 A | | 9/1999 | Vancaillie et al. |
| 6,032,673 A | | 3/2000 | Savage et al. |
| 6,086,542 A | | 7/2000 | Glowa et al. |
| 6,090,123 A | | 7/2000 | Culp et al. |
| 6,113,594 A | | 9/2000 | Savage |
| 6,156,049 A | | 12/2000 | Lovato et al. |
| 6,159,160 A | | 12/2000 | Hsei et al. |
| 6,159,209 A | | 12/2000 | Hakky |
| 6,471,639 B1 | * | 10/2002 | Rudischhauser et al. .... 600/128 |
| 6,626,827 B1 | | 9/2003 | Felix et al. |
| 2003/0130565 A1 | * | 7/2003 | Muller ....................... 600/156 |
| 2005/0043690 A1 | * | 2/2005 | Todd .......................... 604/248 |

FOREIGN PATENT DOCUMENTS

| | | |
|---|---|---|
| DE | 196 33 124 A1 | 5/1997 |
| EP | 0 327 410 | 8/1989 |
| EP | 0 557 044 A1 | 8/1993 |
| GB | 2 093 353 A | 9/1982 |
| WO | 93/07821 | 4/1993 |
| WO | 95/30377 | 11/1995 |
| WO | 96/11638 | 4/1996 |
| WO | 99/11184 | 3/1999 |

OTHER PUBLICATIONS

Model 4537 cannula, "Cannula, Diagnostic For 4mm Arthroscopic," Dwg Nos. 8013521, 8011382, 8013520, 8011381, 8007389, 8011385; 6 pages; sold Aug. 11, 1993.

Model 3869 cannula, "Cannula, Diag. 5.8mm Hi-Flow Dual Rotating, Stopcocks," Dwg Nos. 3869, 8014337, 8007389, 8011381, 8107369; 5 pages; sold Apr. 25, 1990.

Model 4492 cannula, "Cannula, Diag. 5.8mm Hi-Flow Rotatable, Single Valve," Dwg Nos. 4492, 8012885, 8013158, 8107369, 8007389; 5 pages; sold Jan. 13, 1994.

U.S. Appl. No. 09/486,977, filed Mar. 6, 2000, Mark Hans Emanuel, Specification is priority document WO 99/11184.

Copy of International Search Report (8 pages).

Copy of Written Opinion of the International Search Authority (10 pages).

* cited by examiner

ENDOSCOPIC DEVICE

TECHNICAL FIELD

This document relates to endoscopic devices.

BACKGROUND

Endoscopic devices are used for examining and operating on a body site such as a body canal or a hollow organ. Endoscopic devices additionally provide ports for the introduction of surgical instruments and irrigation fluid or for the removal of waste irrigation fluid, blood, or tissue fragments to facilitate the operation. The endoscopic device can be, for example, a hysteroscope for examining the uterine cavity, a cystoscope for examining the urinary tract, or a colonoscope for examining the colon.

In general, a hysteroscope releases fluid to expand the uterine cavity so that the inside of the uterine cavity can be viewed. The hysteroscope also provides a light source that permits viewing of both the inside of the uterine cavity and any openings to and from the uterine cavity. If surgery is to be done, small instruments are inserted through the hysteroscope.

SUMMARY

In one general aspect, an endoscopic device for use at a site within a body includes an inner portion and a sheath surrounding the inner portion. The inner portion defines an operative channel that provides a path for fluid to or from the body site. The inner portion also defines an optical channel. The sheath defines a pressure-sensing channel and a fluid channel that provides a path for fluid to or from the body site. The pressure-sensing channel and the fluid channel are defined between the sheath and the inner portion. The pressure-sensing channel is configured to communicate with a pressure sensor to sense pressure at the body site.

Implementations may include one or more of the following features. For example, the operative channel may provide an inflow path for fluid from a fluid source to the body site, while the fluid channel provides an outflow path for fluid from the body site. The inner portion may include a first cylindrical inner wall that defines the operative channel. The inner portion and the sheath may extend along a longitudinal axis of the device.

The inner portion may include a second cylindrical inner wall that defines the optical channel, which may be enclosed within the inner portion to provide an opening for housing an optical device. The optical channel may be radially symmetric.

The inner portion and the sheath may be integral or separate pieces that interfit. The inner portion may include a circular rim having an outer surface that contacts an inner surface of the sheath at a distal end of the inner portion. The inner portion may include an element that aligns with an element of the sheath. The elements of the inner portion and the sheath may be configured to align the inner portion with the sheath.

The endoscopic device may include a pressure-sensing port that maintains coupling between the pressure sensor and the pressure-sensing channel as the pressure-sensing port is rotated relative to the sheath and about a longitudinal axis of the sheath. The endoscopic device may alternatively or additionally include a fluid port that maintains coupling to the fluid channel of the sheath as the fluid port is rotated relative to the sheath and about a longitudinal axis of the sheath.

The endoscopic device may include a hub surrounding the sheath and including the pressure-sensing port. The hub may be configured to seal to the sheath to couple the pressure sensor to the pressure-sensing channel.

The sheath may define an opening extending from the fluid channel to provide a fluid path to or from the fluid channel through the opening of the sheath. The sheath may contact the inner portion at an end of the inner portion. The sheath may include an end that is flush with a distal end of the inner portion.

The inner portion may include an outer region having a first cylindrical portion with a first outer diameter and a second rim portion attached to the first cylindrical portion and having a second outer diameter larger than the first outer diameter. The fluid channel may be bounded between the first cylindrical portion and the sheath.

The pressure-sensing channel may be spatially segregated from the operative channel, the fluid channel, and the optical channel. The operative channel may be radially symmetric.

The operative channel may provide an outflow path for fluid from the body site. The fluid channel may provide an inflow path for fluid from a fluid source to the body site.

The device may include a hub surrounding and sealing a proximal end of the sheath from external fluids. The hub includes a pressure-sensing port that couples the pressure sensor to the pressure-sensing channel.

In another general aspect, a surgical procedure is performed at a body site. A fluid supply is connected to an endoscopic device. The endoscopic device defines a pressure-sensing channel between a sheath and an inner portion, a first fluid flow path between the sheath and the inner portion, and a second fluid flow path enclosed within the inner portion. A pressure sensor is coupled to the pressure-sensing channel and the endoscopic device is inserted into the body site. An operative device is inserted into an operative channel defined by the inner portion and an optical device is housed in an optical channel defined by the inner portion. Fluid from the fluid supply is irrigated to the body site through one of the fluid flow paths. Fluid from the body site is removed through the other of the fluid flow paths and the pressure at the body site is monitored with a pressure sensor.

In another general aspect, an endoscopic device for use at a site within a body includes a continuous flow endoscope defining a channel for sensing pressure and an outflow path for fluid from the body site. The continuous flow endoscope defines an operative channel that defines an inflow fluid path to the body site and is configured to receive an operative device. The continuous flow endoscope defines an optical channel configured to house an optical device.

In another general aspect, an endoscopic device for use at a site within a body includes an inner portion and a sheath surrounding the inner portion. The inner portion defines an operative channel enclosed within the inner portion. The operative channel provides a path for fluid to and from the body site. The operative channel is configured to receive the operative device. The sheath defines a pressure-sensing channel and a fluid channel that provides a path for fluid to or from the body site. The pressure-sensing channel and the fluid channel are defined between the sheath and the inner portion, and the pressure-sensing channel is configured to communicate with a pressure sensor. A pressure-sensing port maintains coupling between the pressure sensor and the pressure-sensing channel as the pressure-sensing port is rotated relative to the sheath and about a longitudinal axis of the sheath.

In another general aspect, an endoscopic device for use at a site within a body includes an inner portion and a sheath surrounding the inner portion. The inner portion defines an operative channel enclosed within the inner portion. The operative channel provides a path for fluid to or from the body site. The sheath defines a pressure-sensing channel that is configured to communicate with a pressure sensor and a fluid channel that provides a path for fluid to or from the body site. The pressure-sensing channel and the fluid channel are defined between the sheath and the inner portion. The sheath includes an alignment element that aligns with an alignment element of the inner portion.

Aspects of the procedures and devices can include one or more of the following advantages. For example, the endoscopic device enables accurate monitoring of irrigation fluid pressure during a procedure, thus preventing life threatening complications to the patient. Accurate monitoring is particularly critical when non-physiological irrigation and distention fluids, such as 5% sorbitol and 1.5% glycine, are infused into the body site. Non-physiological fluids are frequently used during electrosurgical procedures because these fluids are not electrically conducting. Monitoring of non-physiological fluids is important because excessive uptake of these fluids into the body site during the procedure poses serious risks to the patient such as surgical complications and death.

The amount of fluid uptake by the body at the body site is a function of the pressure that is applied to the body site by the irrigation fluid (called distention). If the body site is a uterine cavity, which is a particularly vascular system, and the endoscopic device is a hysteroscope, fluid uptake occurs relatively easily when the distension pressure exceeds the venous pressure of the cardiovascular system. Thus, measuring or predicting uterine distention pressure accurately is critical to keeping fluid uptake by the body to a minimum to improve safety of hysteroscopic procedures.

The pressure-sensing channel is separated from and does not obstruct the operative channel. Thus, the pressure-sensing channel does not interfere with introduction of the operative device. Additionally, though the inner portion and the sheath contact each other at the rims, concentricity between the inner portion and the sheath is maintained throughout the longitudinal length.

Other features will be apparent from the description, the drawings, and the claims.

DESCRIPTION OF DRAWINGS

Like reference symbols in the various drawings indicate like elements.

DETAILED DESCRIPTION

Referring to FIGS. 1A–1F, an endoscopic device such as a hysteroscope 100 is used to examine and surgically operate on a body site such as a uterine cavity of a patient. The hysteroscope 100 extends along a longitudinal axis 115 and has a distal, cylindrical, end portion 117 for insertion into the uterine cavity, and a proximal end portion 119 for use by an operator external to the uterine cavity. The hysteroscope 100 includes an outer member 125 (FIG. 1E) configured to receive an inner member 140 (FIG. 1D), as discussed below.

By convention, the following definitions are used throughout. First, "inflow" is used to designate fluid that flows through an inlet channel within the hysteroscope 100 and enters the uterine cavity. "Outflow" is used to designate fluid that leaves the uterine cavity and flows through a channel within the hysteroscope 100. An endoscopic device that is "continuous flow" includes a channel for fluid inflow and a channel for fluid outflow. Some endoscopic devices are configured to be continuous flow because access to the body cavity may be limited to the single opening of the body cavity through which the endoscopic device is inserted. Thus, when using a continuous flow endoscopic device, the surgeon need not create an incision into the patient to irrigate fluid from the body site because the fluid is able to flow through the outflow channel of the device.

Figure 1A:
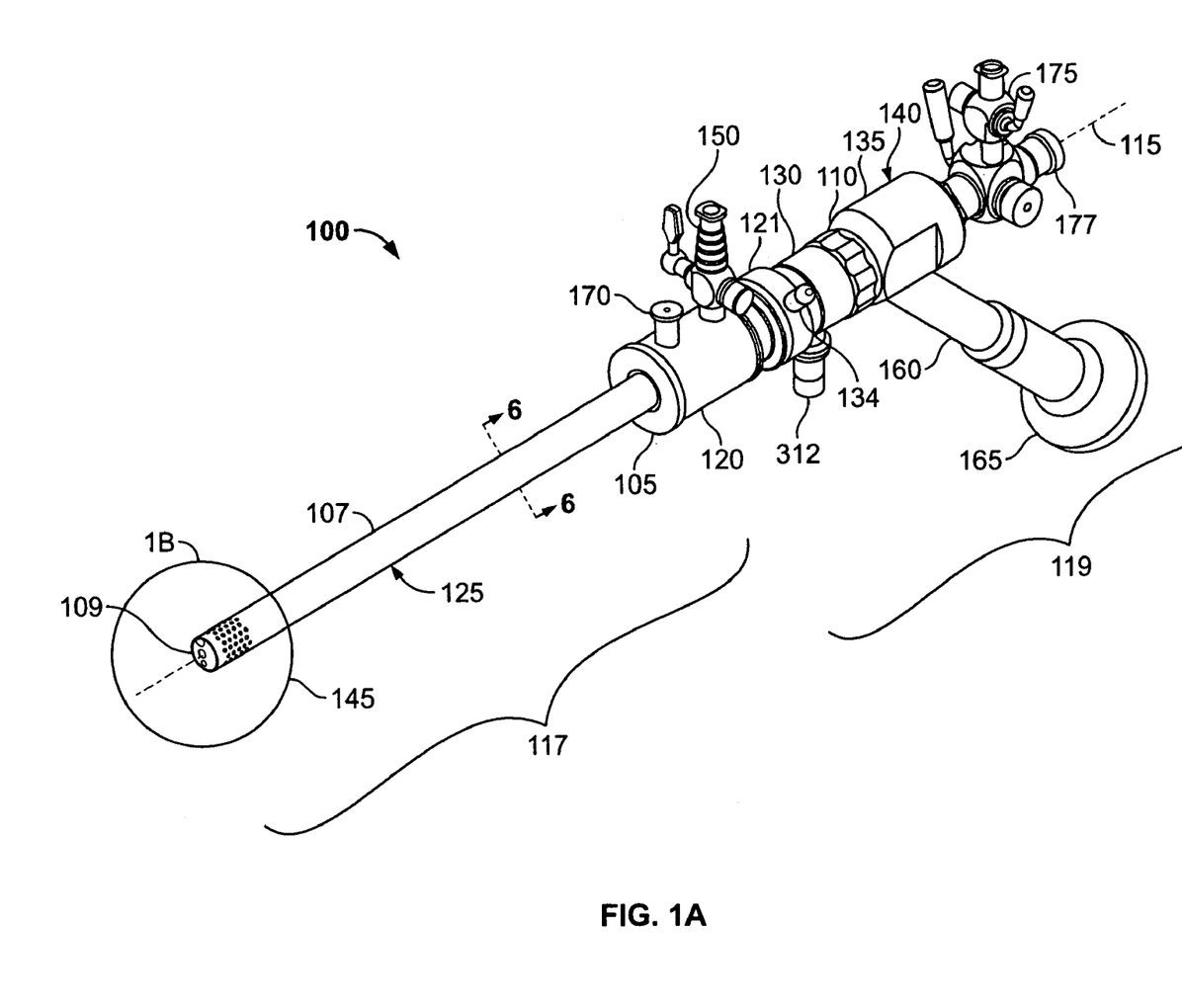
FIG. 1A is a perspective view of an endoscopic device.
Figure 1B:
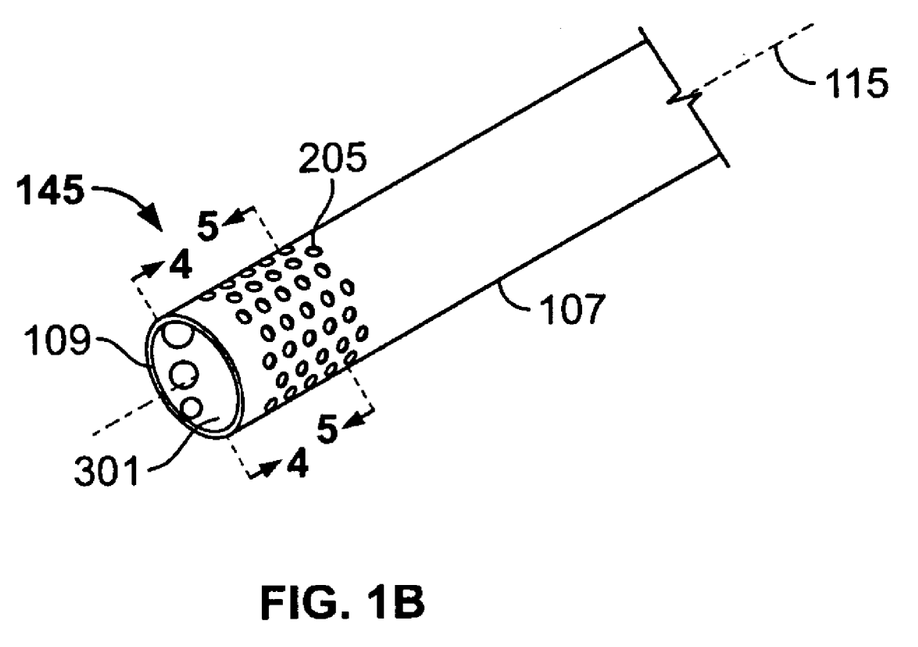
FIG. 1B is an enlarged perspective view of a distal end portion of the endoscopic device of FIG. 1A.
Figure 1C:
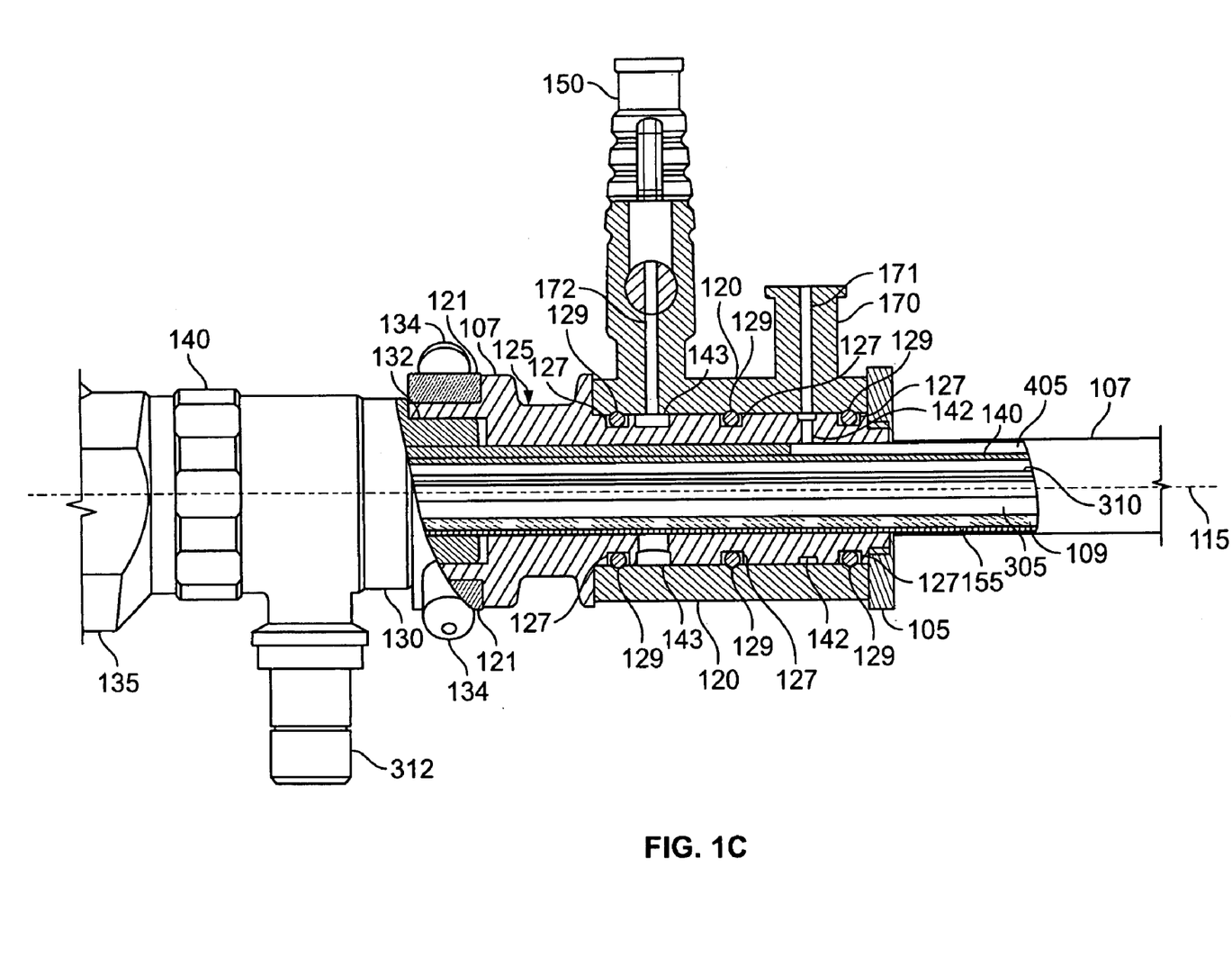
FIG. 1C is a partial cutaway side view of the endoscopic device of FIG. 1A.
Figure 1D:
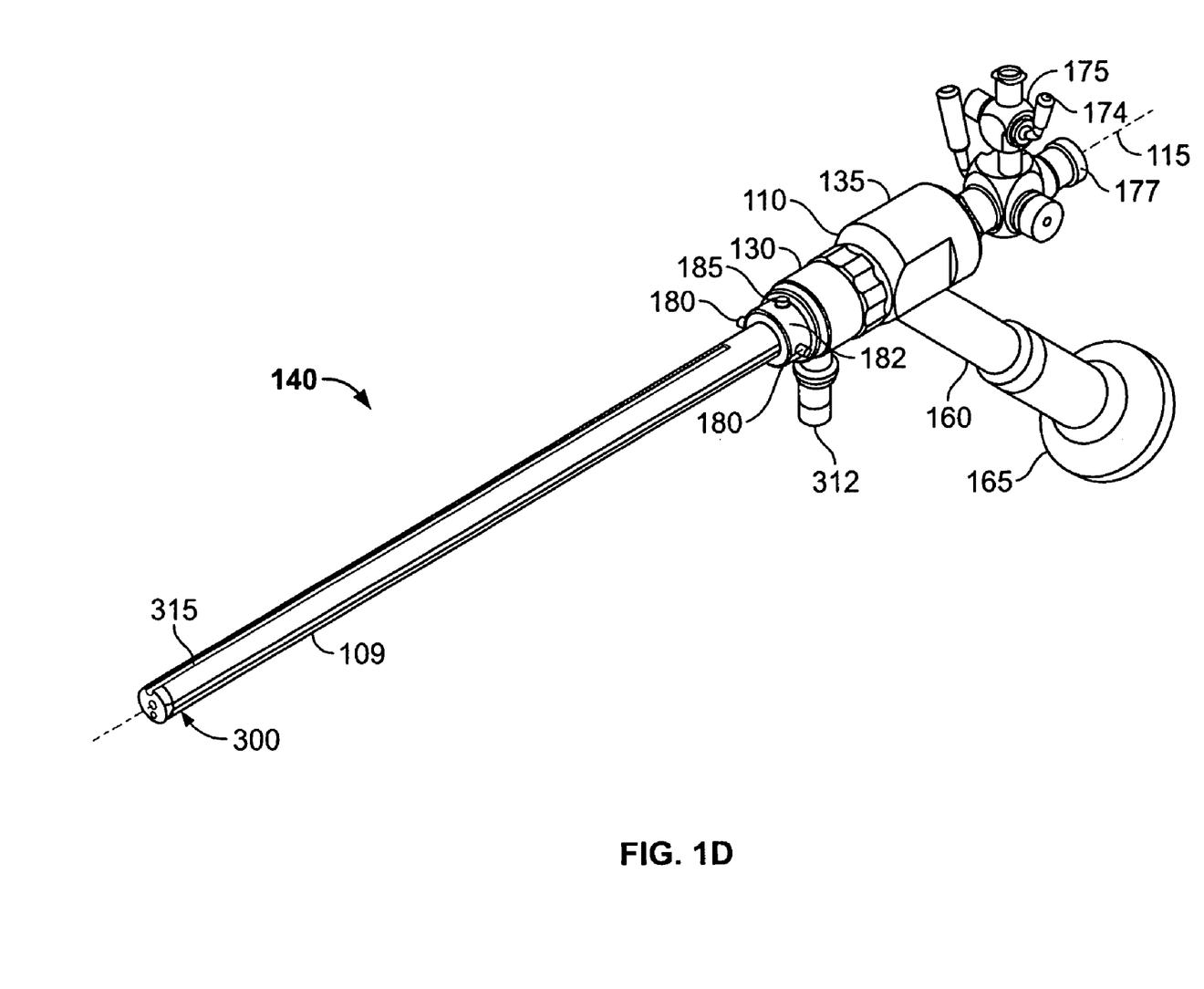
FIG. 1D is a perspective view of an inner member of the endoscopic device of FIG. 1A.
Figure 1E:
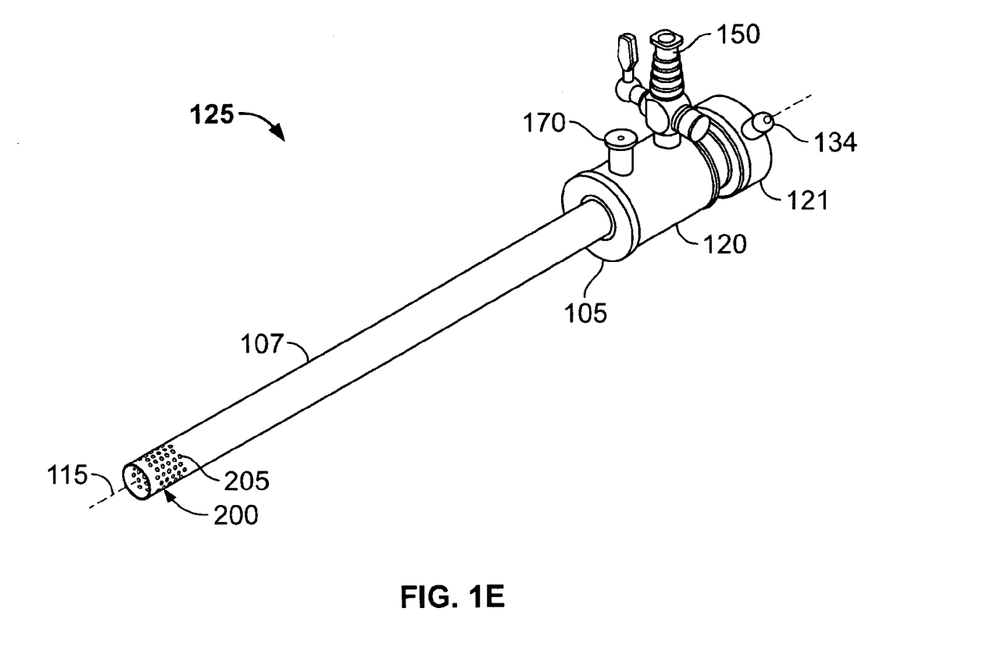
FIG. 1E is a perspective view of an outer member of the endoscopic device of FIG. 1A.

Referring to FIGS. 1C and 1E, the outer member 125 includes a hub 120 and a sheath 107 that extends from the hub 120 distally along the longitudinal axis 115. The sheath 107 and the hub 120 are sealed to prevent unwanted passage of fluid into and out of the hysteroscope 100 and to ensure that fluid freely flows from openings of the sheath 107 through channels and ports of the hub 120, as discussed below. To this end, and with particular reference to FIG. 1C, the sheath 107 includes circumferential grooves 127 for receiving O-rings 129 that seal the hub 120 to the sheath 107.

The hub 120 includes a port 170 and an outflow port 150 that include, respectively, channels 171 and 172 (as shown in FIG. 1C). The sheath 107 includes an opening 142 in fluid communication with the channel 171 of the hub 120 and an opening 143 in fluid communication with the channel 172 of the hub 120. The channels 171 and 172 and the openings 142 and 143 are configured such that the hub 120 can be rotated 360° relative to the sheath 107 while maintaining fluid communication between the channels 171 and 172 and the openings 142 and 143, respectively.

Figure 2:
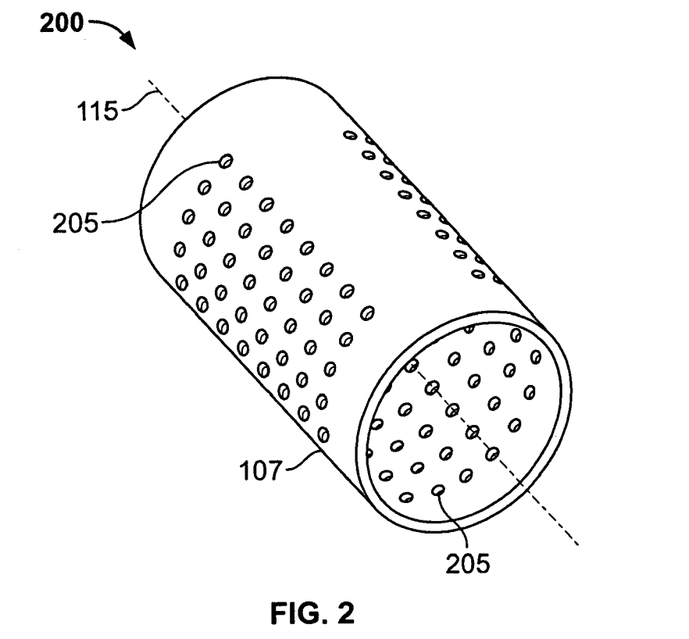
FIG. 2 is a perspective view of a distal end portion of an outer member of the endoscopic device of FIG. 1A.

Referring to FIGS. 1B and 2, the sheath 107 includes a distal portion having circular openings 205 formed along longitudinal rows about the circumferences of the sheath 107. The openings 205 provide channels for fluid outflow during a patient examination or surgical procedure.

Figure 1F:
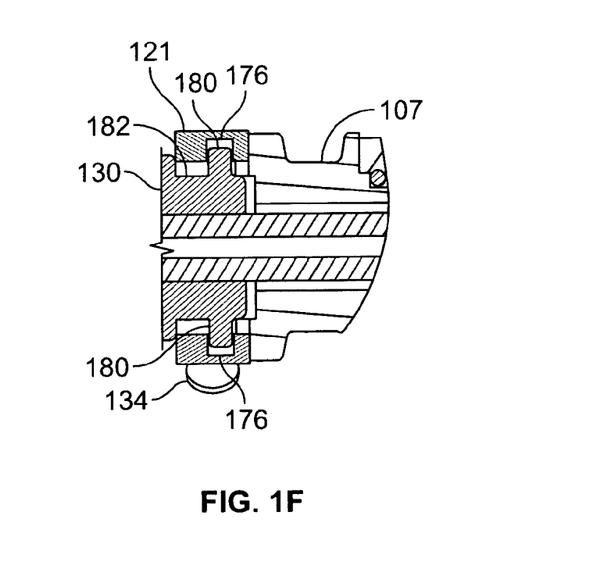
FIG. 1F is a partial cutaway side view of the endoscopic device of FIG. 1A.

Referring particularly to FIGS. 1C, 1E and 1F, the sheath 107 includes a proximal connector 121 having protrusions 134 that enable the user to grip and rotate the connector 121 when joining the outer member 125 to the inner member 140. The proximal connector 121 includes L-shaped channels 176 bored out of an inside surface of the connector 121. Two of the L-shaped channels 176 (shown in FIG. 1F) are spaced apart from each other by 180° and one of the L-shaped channels 176 is spaced from each of the other two by 90°. Each of the L-shaped channels 176 has a proximal side that extends along the longitudinal axis 115 and a distal side extending perpendicularly from the proximal side and the longitudinal axis 115.

As shown in FIG. 1D, the inner member 140 includes a tool member 110 and an inner cylindrical portion 109 that extends from the tool member 110 distally along the longitudinal axis 115. The outer diameter of the inner cylindrical portion 109 is less than the inner diameter of the sheath 107. The inner member 140 is sized to fit within and mate with the outer member 125, as discussed below.

The tool member 110 includes a connector 130 and a tube 135 for receiving operative devices. Guide pins 180 and 185 are formed along an outer surface of a circular rim 182 of the connector 130. The guide pins 180 are spaced apart by 180° and the guide pin 185 is spaced from each of the guide pins 180 by 90°. In addition, the circular rim 182 maintains concentricity between the sheath 107 and the inner cylindrical portion 109 along the longitudinal axis 115 when the inner member 140 and the outer member 125 are assembled.

An optical port 312 is positioned on the connector 130 to receive a light source. Additionally, the tube 135 may couple to a telescope 160 having an eyepiece with an opening that permits the operator to view the cavity directly from the eyepiece 165 or through a camera coupled to the eyepiece 165. The tube 135 includes an inflow port 175 that connects with a source of fluid external to the hysteroscope 100 and an entry port 177 that receives an operative device.

Referring also to FIGS. 3–6, the inner member 140 includes an operative channel 305 and an optical channel 310 extending from a distal portion 300 through the tool member 110. The operative channel 305, which is defined within the inner member 140, extends along the longitudinal axis 115, through the tube 135, and couples to the inflow port 175 and to the entry port 177. The operative channel 305 provides an inlet channel for inflow to the uterine cavity from the inflow port 175. Fluid inflow through the operative channel 305 is controlled by an inflow valve 174 on the inflow port 175. The operative channel 305 is designed to receive an operative device, which has been inserted into the tube 135 through the entry port 177. The operative device is any device that is configured to alter or reconfigure tissue at the body cavity. For example, the operative device may be a laser, a shaver, a cutting device, a drill, a clamp, a grasping device, a staple, or any tissue penetrating device.

The optical channel 310, which is defined within the inner member 140, extends along the longitudinal axis 115, through the tube 135, and couples to the optical port 312. The optical channel 310 is designed to house one or more optical devices, such as a lens for focusing the light from the light source or the uterine cavity, a waveguide for capturing images of the uterine cavity, or a fiber optic bundle that transports light from the light source received through the optical port 312 to the uterine cavity. The lens can be positioned anywhere along the channel 310. The fiber optic bundle may be designed into any suitable form, such as, for example, a hollow ring, a single bundle, or a set of bundles. Additionally, the optical channel 310 may couple with the telescope 160 to permit the operator to view the uterine cavity.

Figure 3:
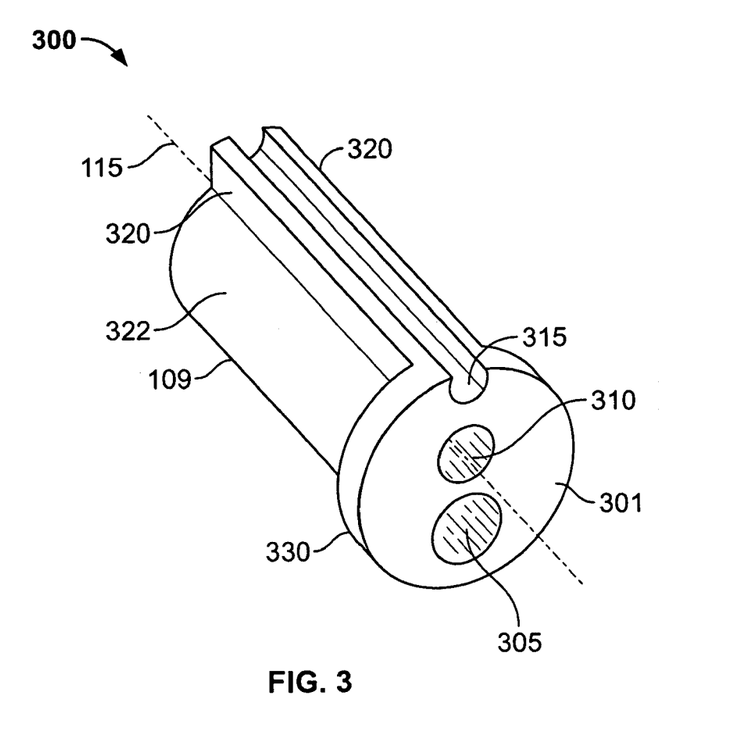
FIG. 3 is a perspective view of a distal end portion of an inner member of the endoscopic device of FIG. 1A.

The inner cylindrical portion 109 includes a groove 315 defined between longitudinal ledges 320 that are formed on an outer surface 322 of the inner cylindrical portion 109 along the longitudinal axis 115. A partially-circular rim 330 is formed along the distal end 301 of the inner member 140. The rim 330 has an outer diameter that is larger than an outer diameter of the outer surface 322.

To assemble the inner member 140 and the outer member 125, the distal portion 300 of the inner member 140 is inserted into the connector 121 of the outer member 125. The operator uses the protrusions 134 to grip and rotate the connector 121 during assembly. As the distal portion 300 is inserted into the connector 121, the inner cylindrical portion 109 slides through the hub 120 and through the sheath 107. Guide pins 180 slide through the proximal side of the L-shaped channels 176 that are spaced apart by 180°. Additionally, the guide pin 185 slides through the proximal side of the L-shaped channel 176 that is positioned between the other two L-shaped channels 176. As the distal portion 300 is further inserted into the outer member 125, the guide pins 180 and 185 reach the edges of the proximal sides of the L-shaped channels 176. At this point, the connector 121 is rotated relative to the outer member 125 and the guide pins 180 and 185 slide through the distal sides of the L-shaped channels 176. The inner member 140 is locked in place within the outer member 125 due to the frictional engagement between the guide pins 180 and the respective L-shaped channels 176. Furthermore, the outer member 125 and the inner member 140 are constrained to join in only one configuration because the guide pins 180 and 185 can move through the L-shaped channels in only one alignment.

Figure 4:
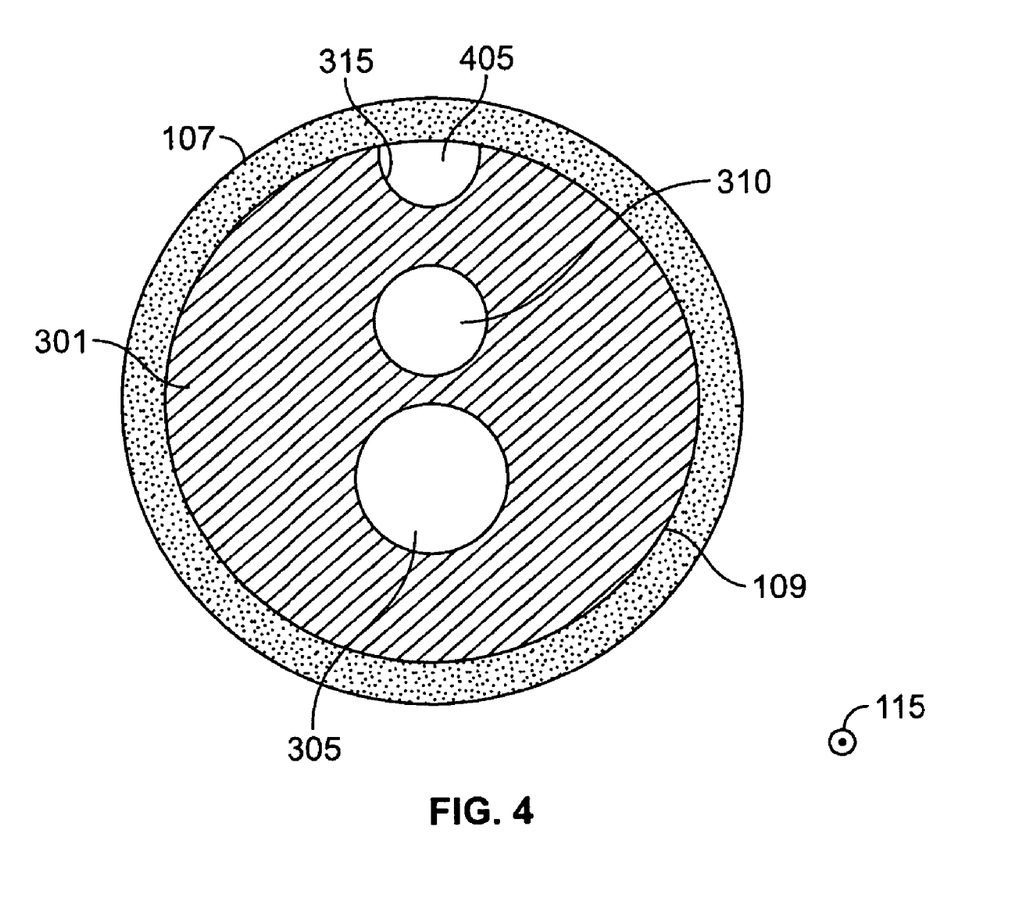
FIG. 4 is a cross-sectional view along line 4—4 of the endoscopic device of FIG. 1B.
Figure 5:
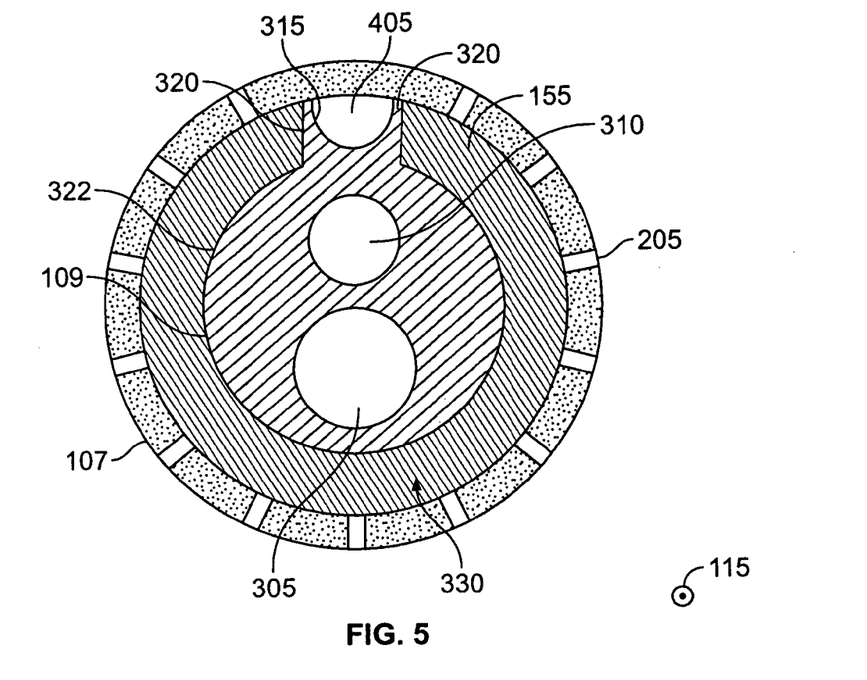
FIG. 5 is a cross-sectional view along line 5—5 of the endoscopic device of FIG. 1B.
Figure 6:
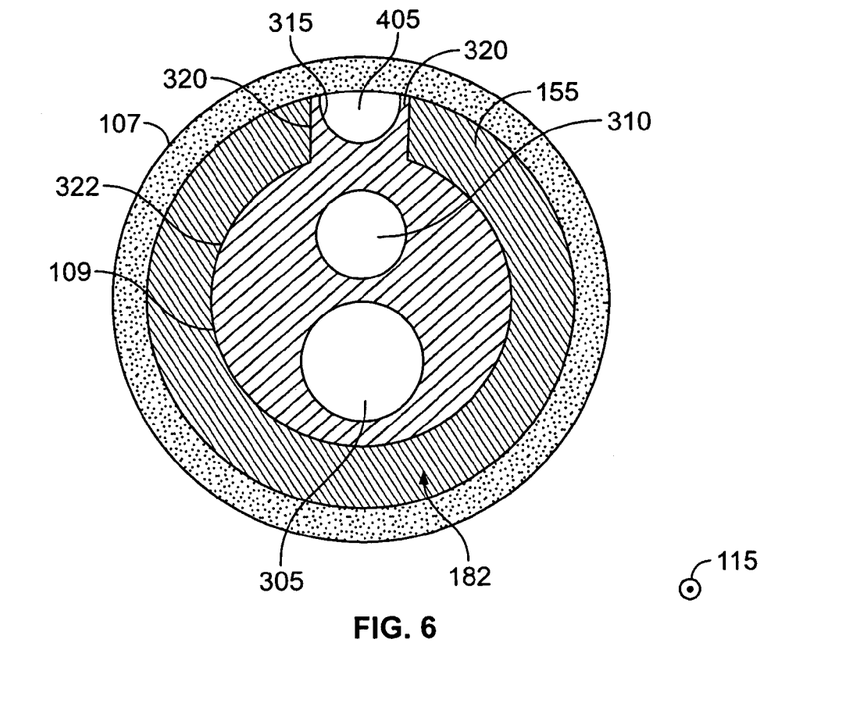
FIG. 6 is a cross-sectional view along line 6—6 of the endoscopic device of FIG. 1A.

Once assembled, the groove 315 and the sheath 107 form a third, pressure-sensing channel 405 along the longitudinal axis 115 between the sheath 107 and the groove 315. A pressure sensor or appropriate pressure sensing apparatus (not shown) is coupled to the port 170 (FIGS. 1A and 1C) and is fluidly connected with the pressure-sensing channel 405 through the channel 171 within the port 170 and the opening 142 of the sheath 107 (as shown in FIG. 1C). In this way, the pressure sensor measures actual pressure at the uterine cavity through the pressure-sensing channel 405. The pressure-sensing channel 405 extends past the opening 142 such that the pressure-sensing channel 405 is fluidly coupled to the opening 142. The opening 142 is designed to extend through the sheath 107 and to communicate with the pressure-sensing channel 405 at one location along the circumference of the sheath 107. As discussed above, the outer member 125 and the inner member 140 align in only one configuration, which ensures that the opening 142 is aligned with the pressure-sensing channel 405. Furthermore, the pressure-sensing channel 405 ends just beyond the opening 142 such that the pressure-sensing channel 405 does not communicate with the opening 143.

An outflow channel 155 is defined along the longitudinal axis 115 between the sheath 107 and the inner cylindrical portion 109. The outflow channel 155 allows fluid to flow from the uterine cavity through the openings 205, through the opening 143 of the sheath 107, and through the channel 172 of the outflow port 150 (shown in FIGS. 1A and 1C). Moreover, outflow fluid from the outflow channel 155 is prevented from entering the pressure-sensing channel 405 and the port 170 because the outflow channel 155 is segregated from the pressure-sensing channel 405 by the longitudinal ledges 320. Fluid outflow through the outflow channel 155, the opening 143, and the channel 172 is controlled by the outflow port 150. The outflow port 150 is adapted to be coupled to an appropriate mechanism (such as a suction device) for removing fluid.

Because the outflow channel 155 and the operative channel 305 are separate, non-communicating channels, resistance to fluid flow within the outflow channel 155 remains constant regardless of the shape or size of the operative device within the operative channel 305. Furthermore, the outflow channel 155 is segregated from and thus does not communicate with the opening 142.

The components of the hysteroscope 100 can be made of materials that are selected to facilitate safety and durability in operation of the hysteroscope. Thus, for example, the inner member 140 and/or the outer member 125 can be made of metal alloys or plastics. Furthermore, the hysteroscope is sized and dimensioned to facilitate viewing the uterine cavity. For example, the sheath 107 has an outer diameter of about 6–11 mm along end portion 117 and a longitudinal length of 15–25 cm, and the overall length of the hysteroscope 100 is about 25–35 cm.

The operator may receive the hysteroscope 100 in two pieces, the outer member 125 and the inner member 140. Thus, the operator would need to assemble the hysteroscope prior to use. During assembly, the operator connects the fluid lines to appropriate ports 150 and 175 and to the pressure-sensing channel 405 through port 170. Additionally, if a surgical procedure is performed, the operator inserts an operative device into the operative channel 305 through the entry port 177. The optical device is housed within the optical channel 310 and the operator need only attach the light source to the optical channel 310 using the port 312.

After assembly, the operator inserts the hysteroscope 100 into the uterine cavity in a patient procedure. The operator guides the end portion 117 of the hysteroscope 100 to a particular location within the uterine cavity using the selected optical devices. During the patient procedure, the operator continuously pumps or irrigates fluid into the uterine cavity through the operative channel 305 to distend the uterine cavity, thus enabling the operator to perform the desired procedure. Moreover, the operator removes fluid and any other debris (such as tissue or blood) from the uterine cavity through the outflow channel 155. Fluid pressure is provided, for example, by positioning a source of fluid at a predetermined height in the operating room relative to the uterine cavity. As another example, fluid pressure may be provided by a pump that has a pre-selected pressure setting.

The hysteroscope is designed to provide fluid flow into and out of the uterine cavity and to provide actual (not estimated) intrauterine pressure information to the operator (or to a pump) to insure that a predetermined pressure limit is not exceeded. This is accomplished by sensing pressure through the pressure-sensing channel 405, which is segregated from the operative channel 305 and the outflow channel 155.

Other implementations are within the scope of the following claims.

For example, the endoscopic device 100 can be designed for use in any body site. The endoscopic device can be a cystoscope for examining a urinary tract or a colonoscope for examining a colon. The openings 205 may be shaped to have non-circular cross-sections, such as, for example, elliptical or polygonal cross-sections.

Figure 7:
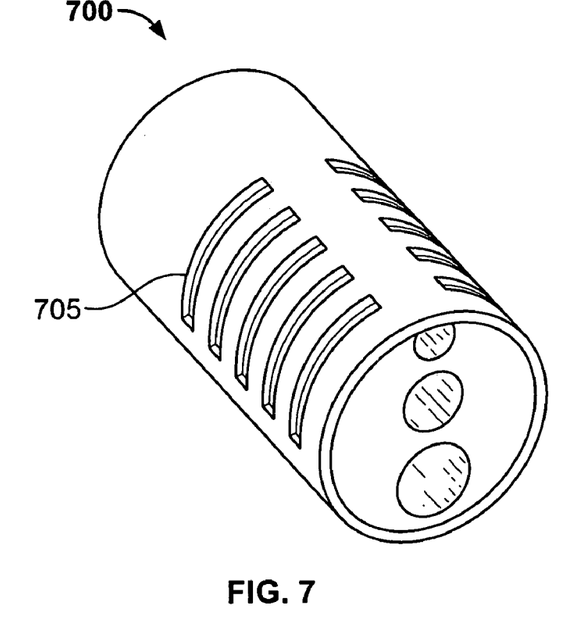
FIGS. 7 and 8 are perspective views of alternative implementations of distal end portions of endoscopic devices.
Figure 8:
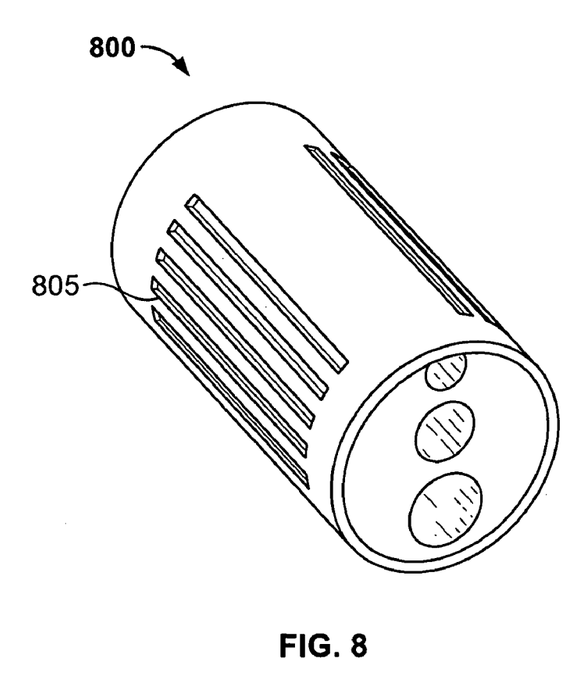

Referring to FIGS. 7 and 8, distal end portions 700 and 800 of alternate implementations of the hysteroscope replace the openings 205 in the outer member with transverse slots 705 and longitudinal slots 805, respectively.

In another implementation, the fluid inflow and outflow paths may be reversed from the description above. Thus, for example, the channel 155 may provide an inflow path for fluid from a source of fluid and the operative channel 305 may provide an outflow path for fluid from the uterine cavity.

Any number of parts of the hysteroscope 100 may be pre-assembled prior to use by the operator. For example, the operator may receive the hysteroscope 100 completely assembled or the operator may need to assemble the hub 120 to the sheath 107 and/or the tool member 110 to the inner cylindrical portion 109. The optical device may arrive separately from the hysteroscope 100. Thus, the operator may need to insert the optical devices into the optical channel 310 upon receipt of or prior to use of the hysteroscope 100.

The inner member 140 may be formed integrally with the outer member 125. Though the connector 121 is described as including L-shaped channels that mate with the guide pins of the inner member 140, the outer member 125 may lock to the inner member 140 using any suitable locking mechanism. For example, the outer member 125 may include guide pins and the inner member 140 may include a channel. As another example, the inner member 140 may include a single protrusion that mates with the channel of the outer member 125.

The pressure sensor may be a miniature pressure sensor that is inserted in the port 170 and/or the channel 405 to measure pressure within the channel 405. Electrical signals from the miniature pressure sensor may be analyzed and/or reviewed using a pressure sensor controller external to the port 170.

The inner cylindrical member 109 and the tube 135 may be formed as an integral piece. Likewise, the sheath 107 and the hub 120 may be formed as an integral piece.

What is claimed is:

1. An endoscopic device for use at a site within a body, the endoscopic device comprising:
    an inner portion defining:
        an operative channel providing a path for fluid to or from the body site; and
        an optical channel; and
    a sheath removably coupled to the inner portion, the sheath surrounding the inner portion to define a pressure-sensing channel and a fluid channel providing a path for fluid to or from the body site, the pressure-sensing channel and the fluid channel being defined between the sheath and the inner portion,
    wherein the pressure-sensing channel is configured to communicate with a pressure sensor, and
    wherein the pressure-sensing channel and the fluid channel are completely segregated to limit fluid communication between the channels.

2. The device of claim 1 wherein the operative channel provides an inflow path for fluid from a fluid source to the body site.

3. The device of claim 2 wherein the fluid channel provides an outflow path for fluid from the body site.

4. The device of claim 1 wherein the operative channel is enclosed within the inner portion and is configured to receive an operative device.

5. The device of claim 1 wherein the inner portion includes a first cylindrical inner wall that defines the operative channel.

6. The device of claim 5 wherein the inner portion includes a second cylindrical inner wall that defines the optical channel and the optical channel is enclosed within the inner portion to provide an opening for housing an optical device.

7. The device of claim 1 wherein the optical channel is radially symmetric.

8. The device of claim 1 wherein the pressure-sensing channel is spatially segregated from the optical channel.

9. The device of claim 1 wherein an element of the inner portion aligns with an element of the sheath.

10. The device of claim 9 wherein the elements are configured to align the inner portion with the sheath.

11. The device of claim 1 wherein the sheath defines an opening extending from the fluid channel to provide a fluid path to or from the fluid channel through the opening of the sheath.

12. The device of claim 1 wherein the sheath contacts the inner portion at a distal end of the inner portion.

13. The device of claim 1 wherein a distal end of the sheath is flush with a distal end of the inner portion.

14. The device of claim 1 wherein the inner portion includes a circular rim having an outer surface that contacts the inner surface of the sheath at a distal end of the inner portion.

15. The device of claim 1 wherein the inner portion includes an outer region having a first cylindrical portion with a first outer diameter and a second rim portion attached to the first cylindrical portion and having a second outer diameter larger than the first outer diameter.

16. The device of claim 15 wherein the fluid channel is bounded between the first cylindrical portion and the sheath.

17. The device of claim 1 wherein the pressure-sensing channel is spatially segregated from the operative channel.

18. The device of claim 1 wherein the operative channel is radially symmetric.

19. The device of claim 1 wherein the operative channel provides an outflow path for fluid from the body site.

20. The device of claim 19 wherein the fluid channel provides an inflow path for fluid from a fluid source to the body site.

21. The device of claim 1 further comprising a pressure-sensing port that maintains coupling between the pressure sensor and the pressure-sensing channel as the pressure-sensing port is rotated relative to the sheath and about a longitudinal axis of the sheath.

22. The device of claim 1 further comprising a fluid port that maintains coupling to the fluid channel of the sheath as the fluid port is rotated relative to the sheath and about a longitudinal axis of the sheath.

23. The device of claim 1 further comprising a hub surrounding and sealing a proximal end of the sheath from external fluids, the hub including a pressure-sensing port that couples the pressure sensor to the pressure-sensing channel.

24. A method of performing a surgical procedure at a body site, the method comprising:
    connecting a fluid supply to an endoscopic device that defines a pressure-sensing channel between a sheath and an inner portion, a fluid flow path between the sheath and the inner portion, and a fluid flow path within the inner portion;
    coupling a pressure sensor to the pressure-sensing channel;
    inserting the endoscopic device into the body site;
    inserting an operative device into an operative channel defined by the inner portion;
    connecting a light source to an optical channel defined by the inner portion and housing an optical device, the operative device being positioned within the operative channel while the optical channel houses the optical device;
    irrigating fluid from the fluid supply to the body site through one of the fluid flow paths;
    removing fluid from the body site through the other of the fluid flow paths; and
    monitoring pressure that is sensed at the pressure sensor.

25. An endoscopic device for use at a site within a body, the endoscopic device comprising:
    a continuous flow endoscope defining:
        an optical channel configured to house an optical device,
        an operative channel configured to receive an operative device while providing an inflow path for receiving fluid from a fluid source and delivering fluid to the body site and while the optical channel houses the optical device,
        an outflow path for fluid from the body site, and
        a channel for sensing pressure,
    wherein the optical channel is positioned outside the operative channel.

26. An endoscopic device for use at a site within a body, the endoscopic device comprising:
    an inner portion defining an operative channel enclosed within the inner portion and providing a path for fluid to and from the body site, the operative channel being configured to receive an operative device;
    a sheath surrounding the inner portion to define a pressure-sensing channel and a fluid channel providing a path for fluid to or from the body site, the pressure-sensing channel and the fluid channel being defined between the sheath and the inner portion, the pressure-sensing channel being configured to communicate with a pressure sensor; and
    a pressure-sensing port that maintains coupling between the pressure sensor and the pressure-sensing channel as the pressure-sensing port is rotated relative to the sheath and about a longitudinal axis of the sheath.

27. An endoscopic device for use at a site within a body, the endoscopic device comprising:
    an inner portion defining an operative channel enclosed within the inner portion and providing a path for fluid to or from the body site, the inner portion including an alignment element; and
    a sheath surrounding the inner portion to define a pressure-sensing channel and a fluid channel providing a path for fluid to or from the body site, the pressure-sensing channel and the fluid channel being defined between the sheath and the inner portion, the sheath including an alignment element that aligns with the alignment element of the inner portion such that in use, when assembling the inner portion and the sheath, the alignment elements align the inner portion and the sheath;
    wherein the pressure-sensing channel is configured to communicate with a pressure sensor, and
    wherein the pressure-sensing channel and the fluid channel are completely segregated to limit fluid communication between the channels.

28. The device of claim 26 wherein the inner portion and the sheath are integral.

29. The device of claim 26 wherein the inner portion and the sheath are separate pieces that interfit.

30. An endoscopic device for use at a site within a body, the endoscopic device comprising:
    an inner portion defining:
        an operative channel configured to receive an operative device while providing a path for at least receiving fluid from a fluid source and delivering fluid to the body site; and
        an optical channel, the optical channel being positioned outside the operative channel; and
    a sheath surrounding the inner portion to define a pressure-sensing channel and a fluid channel providing a path for fluid to or from the body site, the pressure-sensing channel and the fluid channel being defined by the sheath and the inner portion, wherein the pressure-sensing channel is configured to communicate with a pressure sensor.

31. An endoscopic device for use at a site within a body, the endoscopic device comprising:

an inner portion defining:

an operative channel providing a path for fluid to or from the body site; and an optical channel, the inner portion including an outer region having a first cylindrical portion with a first outer diameter; and a sheath surrounding the inner portion to define a pressure-sensing channel and a fluid channel providing a path for fluid to or from the body site, the pressure-sensing channel being defined between the sheath and the inner portion, the fluid channel being bounded between the first cylindrical portion and the sheath, wherein the pressure-sensing channel is configured to communicate with a pressure sensor, wherein the pressure-sensing channel and the fluid channel are completely segregated to limit fluid communication between the channels.

32. The endoscopic device of claim 31, wherein the inner portion further includes a second rim portion attached to the first cylindrical portion and having a second outer diameter larger than the first outer diameter.

* * * * *